United States Patent [19]

Horowitz

[11] Patent Number: 4,841,023
[45] Date of Patent: * Jun. 20, 1989

[54] INACTIVATION OF VIRUSES IN LABILE PROTEIN-CONTAINING COMPOSITIONS USING FATTY ACIDS

[75] Inventor: Bernard Horowitz, New Rochelle, N.Y.

[73] Assignee: New York Blood Center, Inc., New York, N.Y.

[*] Notice: The portion of the term of this patent subsequent to Sep. 23, 2003 has been disclaimed.

[21] Appl. No.: 878,446

[22] Filed: Jun. 25, 1986

[51] Int. Cl.$^4$ .................... A61K 39/18; A61K 39/29
[52] U.S. Cl. ........................ 530/351; 424/89; 424/101; 435/212; 435/215; 530/350; 530/362; 530/363; 530/364; 530/369; 530/380; 530/381; 530/382; 530/383; 530/384; 530/385; 530/389; 530/373; 530/395; 530/399; 530/410; 530/808; 530/809
[58] Field of Search .............. 424/89, 101; 530/382, 530/383, 410, 381, 384, 389, 350, 380, 393, 751, 385, 399, 362, 363, 364, 369, 808, 809; 435/212, 215

[56] References Cited

U.S. PATENT DOCUMENTS

| | | |
|---|---|---|
| 3,100,737 | 8/1963 | Auerswald et al. ............ 530/364 X |
| 3,497,492 | 2/1970 | Buck et al. .................... 530/364 X |
| 3,636,196 | 1/1972 | Bauer et al. ..................... 424/89 |
| 3,651,211 | 3/1972 | Gilichriest et al. ................ 424/89 |
| 3,655,871 | 4/1972 | Werner ............................ 424/89 |
| 3,660,234 | 5/1972 | Gray ............................. 424/89 X |
| 3,847,737 | 11/1974 | Kanarelt ......................... 424/89 |
| 3,926,939 | 12/1975 | Ivanov et al. .................. 530/364 |
| 3,962,421 | 6/1976 | Neurath .......................... 424/89 |
| 3,983,229 | 9/1976 | Relyveld ......................... 424/92 |
| 3,992,367 | 11/1976 | Plan et al. .................... 530/369 X |
| 4,036,952 | 7/1977 | Bauer et al. ..................... 424/89 |
| 4,070,454 | 1/1978 | Relyveld ......................... 424/89 |
| 4,083,958 | 4/1978 | Bryans ........................... 424/89 |
| 4,156,681 | 5/1979 | Schneider et al. ................ 530/364 |
| 4,177,188 | 12/1979 | Hansen ........................... 530/364 |
| 4,178,126 | 12/1979 | Weep ............................ 416/17 |
| 4,314,997 | 2/1982 | Shanbrom ...................... 514/21 X |
| 4,315,919 | 2/1982 | Shanbrom ..................... 424/101 X |
| 4,350,707 | 9/1982 | Keith ............................ 424/89 X |
| 4,370,264 | 1/1983 | Kotitschke et al. ............... 530/381 |
| 4,412,985 | 11/1983 | Shanbrom ...................... 424/88 X |
| 4,424,206 | 1/1984 | Ohmura et al. .................. 424/101 |
| 4,440,679 | 4/1984 | Fernandes et al. ............ 530/382 X |
| 4,481,189 | 11/1984 | Prince ........................... 424/101 |
| 4,540,573 | 9/1985 | Neurath et al. ................. 424/85 X |
| 4,581,231 | 4/1986 | Purcell et al. .................. 424/101 |
| 4,591,505 | 5/1986 | Prince ........................... 424/101 |
| 4,613,501 | 9/1986 | Horowitz ......................... 424/89 |
| 4,720,385 | 1/1988 | Lembach ...................... 530/364 X |
| 4,754,019 | 6/1988 | Gion et al. ..................... 530/364 |
| 4,764,369 | 8/1988 | Neurath et al. .................. 424/89 |

OTHER PUBLICATIONS

Hackh's Chemical Dictionary, 4th Ed. 1980, p. 261.
G. Norkrans et al., *Vox Sang.*, 41, 129 (1981).
M. L. Fletcher, J. M. Trowell, J. Craske, K. Pavier, C. R. Rizza, Br. Med. J., 287, 1754 (1983).
M. J. Alter, *Morbidity and Mortality Weekly Report; Surveillance Summaries*, 32, 23SS (1983).
R. J. Gerety, D. L. Aronson, *Transfusion*, 22, 347 (1982).
E. Vilmer et al., *Lancet*, i, 753 (1984).
B. L. Evatt, D. P. Francis, M. F. T. McLane et al., *Lancet*, ii, 695 (1983).
J. Schupbach et al., *Science*, 224, 500 (1984).
M. G. Sarngadharan, M. Popovic, L. Bruch, J. Schupbach, R. C. Gallo, Science, 224, 506 (1984).

(List continued on next page.)

Primary Examiner—Howard E. Schain
Attorney, Agent, or Firm—Sprung Horn Kramer & Woods

[57] ABSTRACT

There is disclosed a process for rendering a labile protein-containing composition, substantially free of lipid-containing viruses without incurring substantial protein denaturation comprising contacting said composition with an effective amount of a fatty acid or a soluble ester, alcohol or a salt thereof for a sufficient period of time to inactivate virus contained therein.

28 Claims, 2 Drawing Sheets

OTHER PUBLICATIONS

S. J. Feinstone, et al., *Infect. Immun.,* 41, 816 (1983).
A. M. Prince et al., *Vox Sang.,* 46, 36 (1984).
D. W. Bradley, J. E. Maynard, H. Popper et al., *J. Infect. Dis.,* 148, 254 (1983).
R. S. Lane, *Lancet,* ii, 974 (1983).
A. M. L. Lever, A. D. B. Webster, D. Brown, H. C. Thomas, *Lancet,* i, 587 (1985).
H. D. Ochs, S. H. Fischer, F. S. Virant et al., *Lancet,* i, 404 (1985).
A. M. Prince, M. P. J. Piet, B. Horowitz, *New England J. Med.,* 314, 186 (1986).
M. A. Wells et al., *Transfusion,* 26, 210 (1986).
N. Heimburger et al., *Du Gelben Hefte,* 20, 165, (1980).
M. Colombo et al., *Lancet,* i, 1 (1985).
F. E. Preston, C. R. M. Hay, M. S. Dewar, M. Greaves, D. R. Triger, Lancet, ii, 213 (1985).
P. B. A. Kernoff et al., *Lancet,* ii, 721 (1985).
P. M. Mannucci, M. Colombo, F. Rodeghiero, *Lancet,* ii, 1013 (1985).
F. B. Hollinger, G. Dolana, W. Thomas, F. Gyorkey, *J. Infect.* Dis., 150, 250 (1984).
R. H. Purcell et al., *Hepatology,* 5, 1091 (1985).
B. Horowitz, M. E. Wiebe, A. Lippin, J. Vandersande, M. H. Stryker, *Transfusion,* 25, 523 (1985).
B. Horowitz, M. E. Wiebe, A. Lippin, M. H. Stryker, *Transfusion,* 25, 516 (1985).
C. C. Strock, T. Francis, Jr., *J. Exp. Med,* 71, 661 (1940).
A. Kohn, J. Gitelman, M. Inbar, *Arch. Virology,* 66, 301 (1980).
W. Snipes, S. Person, A. Keith, J. Cupp, *Science,* 188, 64 (1975).
J. Sands, D. Auperin, W. Snipes, *Antimicorbial Agents and Chemotherapy,* 15 67 (1979).
J. C. Hierholzer, J. J. Karbara, *J. Food Safety,* 4, 1 (1982).
*Toxic Substance List,* H. E. Christensen (Ed.), 1974, p. 543.
Jefferson and Necheles, *Proc. Soc. Exptl, Biol. Med.,* 68, 248 (1948).

FIG. 3
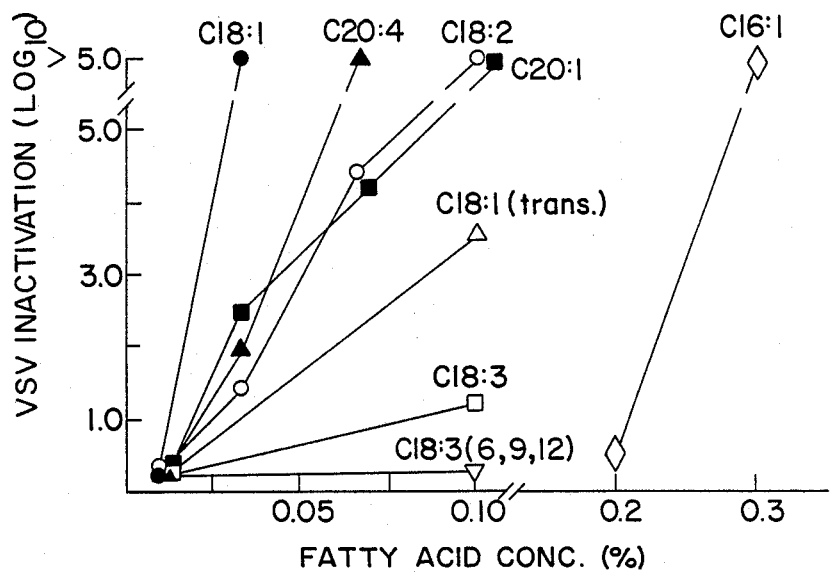
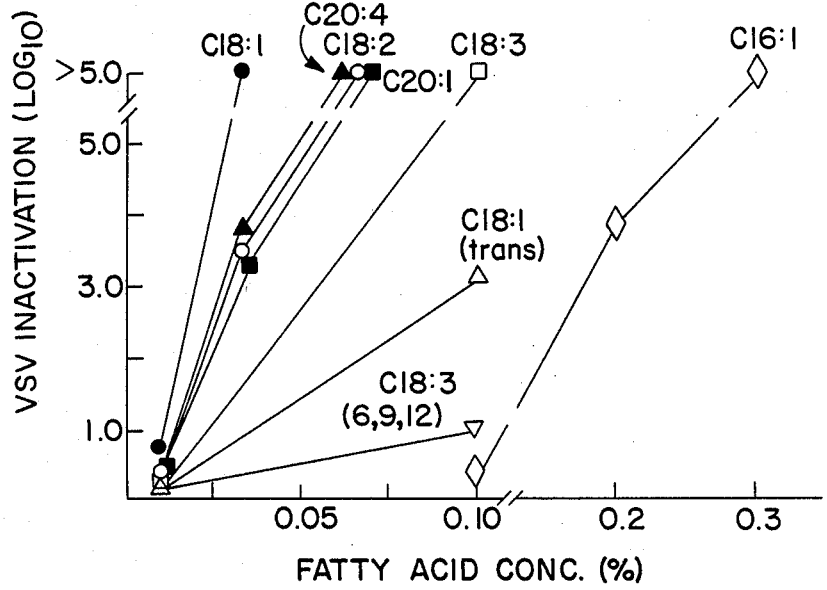
FIG. 4

INACTIVATION OF VIRUSES IN LABILE PROTEIN-CONTAINING COMPOSITIONS USING FATTY ACIDS

CROSS-REFERENCE TO RELATED APPLICATION

This application is a continuation-in-part application of patent application Ser. No. 684,513, filed Dec. 21, 1984, now U.S. Pat. No. 4,613,501.

BACKGROUND OF THE INVENTION

Field of the Invention

This invention relates to undenatured virus-free biologically active protein-containing compositions. More especially, this invention relates to the inactivation of viruses, especially lipid coated viruses, e.g., hepatitis B, in human blood, blood components, blood plasma or any fraction, concentrate or derivative thereof containing blood proteins or non-blood sources including normal or cancer cells, the exudate from cancer or normal cells grown in cultures, hybridomas, in products from gene splicing (DNA), etc., by the use of a fatty acid or an ester or salt thereof or by the use of a long chain unsaturated monoglyceride. In particular, this invention relates to blood plasma or other plasma protein-containing compositions which are rendered substantially free of hepatitis B and/or non-A and non-B hepatitis or other viral infectivity, such blood plasma or fractions thereof having valuable labile proteins, such as, for example, factor VIII, by using fatty acids or long chain unsaturated monoglycerides.

Background Information

Blood derivatives, such as antihemophilic factor concentrate (AHF) and prothrombin complex concentrate (PCC), as traditionally prepared, carry substantial risk of transmitting hepatitis B (HB), non-A, non-B hepatitis (NANBH) and acquired immunodeficiency syndrome (AIDS) (G. Norkrans et al, *Vox Sang.*, 41, 129 (1981); M. L. Fletcher, J. M. Trowell, J. Craske, K. Pavier, C. R. Rizza, *Br. Med. J.*, 287, 1754 (1983); M. J. Alter, *Morbidity and Mortality Weekly Report; Surveillance Summaries*, 32, 23SS (1983); R. J. Gerety, D. L. Aronson, *Transfusion*, 22, 347 (1982); E. Vilmer et al, *Lancet*, i, 753 (1984); B. L. Evatt, D. P. Francis, M. F. T. McLane et al, *Lancet*, ii, 698 (1983); J. Schupbach et al, *Science*, 224, 500 (1984); and M. G. Sarngadharan, M. Popovic, L. Bruch, J. Schupbach, R. C. Gallo, *Science*, 224, 506 (1984). Each of these diseases is associated with lipid-enveloped viruses (S. M. Feinstone et al, *Infect. Immun.*, 41, 816 (1983) and A. M. Prince et al *Vox Sang.*, 46, 36 (1984) though one form of NANBH virus isolated from chimpanzee serum appears to have been protein enveloped (D. W. Bradley, J. E. Maynard, H. Popper et al, *J. Infect. Dis.*, 148, 254 (1983)). Protein enveloped forms of NANBHV were not found in 13 lots of AHF concentrate.

The transmission of non-A, non-B hepatitis also has been associated with at least some preparations of intravenous gamma globulin solutions (R. S. Lane, *Lancet*, ii, 974 (1983); A. M. L. Lever, A. D. B. Webster, D. Brown, H. C. Thomas, *Lancet*, i, 587 (1985); H. D. Ochs, S. H. Fischer, F. S. Virant et al, *Lancet*, i, 404 (1985)). The safety of these solutions with regard to AIDS transmission has been the subject of recent analysis. Though little or no inactivation of the AIDS virus, HTLV-III/LAV, occurs on exposure to the cold ethanolic conditions used in the preparation of IgG (A. M. Prince, M. P. J. Piet, B. Horowitz, *New England J. Med.*, 314, 186 (1986)), the virus appears to separate from this fraction with high efficiency (M. A. Wells et al, *Transfusion*, 26, 210 (1986)) on laboratory scale and the preponderance of clinical data suggests that this product is safe with regard to AIDS transmission.

The development of methods which render blood products safe from virus transmission requires the identification of conditions which are virucidally potent, but which have little effect on protein structure and function. Pasteurization of AHF under a variety of conditions has led to mixed results with regard to virus safety (N. Heimburger et al, *DU gelben Hefte*, 20, 165, (1980); M. Colombo et al, *Lancet*, i, 1 (1985); F. E. Preston, C. R. M. Hay, M. S. Dewar, M. Greaves, D. R. Triger, *Lancet*, ii, 213 (1985); P. B. A. Kernoff et al *Lancet*, ii, 721 (1985); P. M. Mannucci, M. Colombo, F. Rodeghiero, *Lancet*, ii, 1013 (1985); F. B. Hollinger, G. Dolana, W. Thomas, F. Gyorkey, *J. Infect. Dis.*, 150, 250 (1984); and R. H. Purcell et al, *Hepatology*, 5, 1091 (1985)) and has led to alteration of protein structure (B. Horowitz, M. E. Wiebe, A. Lippin, J. Vandersande, M. H. Stryker, *Transfusion*, 25, 523 (1985)).

Numerous attempts have been made to inactivate viruses such as hepatitis B virus (HBV) in mammalian, especially human, blood plasma. It is the practice in some countries to effect inactivation of the hepatitis B virus in the blood plasma by contacting the plasma with a viral inactivating agent of the type which crosslinks with the proteinaceous portion of hepatitis B virus, or which interacts with the nucleic acid of the virus. For instance, it is known to attempt to inactivate hepatitis B virus by contact with an aldehyde, such as formaldehyde, whereby crosslinking to the protein is effected and the hepatitis B virus is inactivated. It is also known to effect inactivation of the virus by contact with beta-propiolactone (BPL), an agent which acts on the nucleic acid of the virus. It is further known to use ultraviolet (UV) light, especially after a beta-propiolactone treatment.

Other inactivating agents include lower alkyl esters of acetic acid for inactivation of flu virus (U.S. Pat. No. 3,655,871); glutaraldehyde (U.S. Pat. No. 3,983,229 and U.S. Pat. No. 4,070,454); tri-n-butyl-phosphate for inactivation of flu virus (U.S. Pat. No. 3,962,421); butylated-hydroxytoluene (U.S. Pat. No. 4,350,707); sulfhydryl (U.S. Pat. No. 3,651,211); ethyleneimine (U.S. Pat. No. 3,636,196 and U.S. Pat. No. 4,036,952); beta-propiolactone combined with acetylethylenimine (U.S. Pat. No. 4,083,958) and tannin (U.S. Pat. No. 4,178,126). Detergents have also been disclosed as viral inactivating agents (U.S. Pat. Nos. 4,314,997 and 4,315,919). Microwaves have also been proposed and disclosed in U.S. Pat. No. 3,660,234. U.S. Pat. No. 4,424,206 discloses the use of heat. Various chlorinated hydrocarbons such as tetrachloroethylene have been proposed for the inactivation of myxoviruses (U.S. Pat. No. 3,847,737).

Unfortunately, viral inactivity agents often alter, denature or destroy valuable protein components, especially so-called "labile" blood coagulation factors of the plasma under conditions required for effective inactivation of virus infectivity. For instance, in heretofore used inactivation processes, factor VIII is inactivated or denatured to the extent of 50–90% or more of the factor VIII present in the untreated plasma. Because of the denaturing effects of these virus inactivating agents, it is necessary in the preparation of derivatives for administration to patients to concentrate large quantities of plasma so that the material to be administered to the patient once again has a sufficient concentration of the undenatured protein for effective therapeutic treatment. This concentration, however, does not affect reduction of the amount of denatured protein. As a result, the patient not only receives the undenatured protein, but a quantity of denatured protein often many times that of the undenatured protein.

For instance, in the inactivation of hepatitis B virus in human blood plasma by beta-propiolactone, there is obtained as a result thereof, a plasma whose factor VIII has been 75% inactivated. The remaining 25% of the factor VIII is, therefore, present in such a small concentration, as a function of the plasma itself, that it is necessary to concentrate large quantities of the factor VIII to provide sufficient concentration to be of therapeutic value. Since such separation techniques do not efficiently remove denatured factor VIII from undenatured factor VIII, the material administered to the patient may contain more denatured protein than undenatured protein. Obviously, such inactivation is valuable from a standpoint of diminishing the risk of hepatitis virus infection. However, it requires the processing of large quantities of plasma and represents significant loss of valuable protein components. Furthermore, administration of large amounts of denatured proteins may render these antigenic to the host and thus give rise to autoimmune diseases, or perhaps, rheumatoid arthritis.

The loss of these valuable protein components is not limited to factor VIII, one of the most labile of the valuable proteins in mammalian blood plasma. Similar protein denaturation is experienced in respect of the following other valuable plasma components: coagulation factors II, VII, IX, X; plasmin, fibrinogen (factor I) IgM, hemoglobin, interferon, etc.

Factor VIII, however, is denatured to a larger extent than many of the other valuable proteins present in blood plasma.

As a result of the foregoing, except in the processing of serum albumin (a stable plasma protein solution which can withstand pasteurization) it was largely the practice in the United States in respect of the processing of blood proteins to take no step in respect of the sterilization for inactivation of viruses. As a result, recipients of factor VIII, gamma-globulin, factor IX, fibrinogen, etc., accepted the risk that the valuable protein components being administered may be contaminated with hepatitis viruses, as well as other infectious viruses. As a result, these recipients faced the danger of becoming infected by these viruses and having to endure the damage which the virus causes to the liver and other organ systems and consequent incapacitation and illness, which may lead to death.

The BPL/UV inactivation procedure discussed above has not so far been adopted in the United States for numerous reasons, one of which lies in the fact that many researchers believe that BPL is itself deleterious since it cannot be removed completely following the inactivation and thus may remain in plasma and plasma derivatives. BPL has been shown to be carcinogenic in animals and is dangerous even to personnel handling it.

Other methods for the inactivation of hepatitis B virus in plasma are known, but are usually impractical. One method involves the addition of antibodies to the plasma whereby an immune complex is formed. The expense of antibody formation and purification add significantly to the cost of the plasma production; furthermore, there is no assurance that a sufficient quantity of hepatitis B or non-A, non-B virus is inactivated. There is currently no test for non-A, non-B antibodies (although there is a test for the virus); hence, it is not possible to select plasma containing high titers of anti-non-A, non-B antibody.

It is to be understood that the problems of inactivation of the viruses in plasma are distinct from the problems of inactivation of the viruses themselves due to the copresence of the desirable proteinaceous components of the plasma. Thus, while it is known how to inactivate the hepatitis B virus, by using crosslinking agents, for example, glutaraldehyde, nucleic acid reacting chemicals, for example, BPL or formaldehyde, or oxidizing agents, for example, chlorox, etc., it has been believed that these methods are not suitable for the inactivation of the virus in plasma due to the observation that most of these inactivating agents (sodium hypochlorite, formaldehyde, beta-propiolactone) denatured the valuable proteinaceous components of the plasma.

U.S. Pat. No. 4,315,919 to Shanbrom describes a method of depyrogenating a proteinaceous biological or pharmaceutical product by contacting such proteinaceous product with a non-denaturing amphiphile.

U.S. Pat. No. 4,314,997 to Shanbrom describes a method of reducing pyrogenicity, hepatitis infectivity and clotting activation of a plasma protein product by contacting the product with a non-denatured amphiphile.

Both Shanbrom U.S. Pat. No. 4,315,919 and U.S. Pat. No. 4,314,997 of a non-ionic detergent, for example, "TWEEN 80" as the amphilphile. It is shown in U.S. Pat. No. 4,540,573 that treatment with "TWEEN 80" by itself is relatively ineffective as a viral inactivating agent.

U.S. Pat. No. 3,962,421 describes a method for the disruption of infectious lipid-containing viruses for preparing sub-unit vaccines by contacting the virus in an aqueous medium with a wetting agent and a trialkylphosphate. Such aqueous medium is defined as allantonic fluid, tissue culture fluid, aqueous extract or a suspension of central nervous system tissue, blood cell eluate and an aqueous extract or suspension of fowl embryo. The patent does not describe hepatitis, nor is it concerned with preparation of blood derivatives containing labile blood protein substantially free of viral infectivity. It is concerned only with disrupting the envelope of lipid-containing viruses for the production of vaccines and not with avoiding or reducing protein denaturation en route to a blood derivative. Tri(n-butyl)phosphate (TNBP) /detergent mixture appear to be both virucidally potent and highly specific (B. Horowitz, M. E. Wiebe, A. Lippin, M. H. Stryker, *Transfusion*, 25, 516 (1985)); however transmission studies in man have just begun.

Problems may also exist in deriving valuable proteins from non-blood sources. These sources include, but are not limited to, mammalian milk, ascitic fluid, saliva, placenta extracts, tissue culture cell lines and their extracts, including transformed cells, and products of fermentation. For instance, human lymphoblastoid cells have been isolated are used to produce alpha interferon. However, the cell line in commercial use today contains Epstein-Barr virus genes. It has been a major concern that the use of interferon produced by these cells would transmit viral infection or induce viral caused cancerous growth.

Unsaturated fatty acids have been shown previously to inactivate lipid enveloped viruses added to buffer solutions and tissue culture media (C. C. Stock, T. Francis, Jr., *J. Exp. Med.*, 71, 661 (1940), A. Kohn, J. Gitelman, M. Inbar, *Arch. Virology*, 66, 301 (1980)). Other hydrocarbons such as butylated hydroxytoluene (W. Snipes, S. Person, A. Keith, J. Cupp, *Science*, 188, 64 (1975)) and long chain alcohols and monoglycerides (J. Sands, D. Auperin. W. Snipes, *Antimicrobial Agents and Chemotherapy*, 15, 67 (1979)) also have antiviral activity. Protein enveloped viruses are unaffected by these treatments (J. C. Hierholzer, J. J. Kabara, *J. Food Safety*, 4, 1 (1982)).

Unsaturated fatty acids are naturally occurring and have low toxicity. (*Toxic Substance List*, H. E. Christensen (Ed.), 1974, p. 543; Jefferson and Necheles, *Proc. Soc. Exptl. Biol. Med.*, 68, 248 (1948)).

SUMMARY OF THE INVENTION

The present invention is directed to achieving three goals, namely, (1) a safe, (2) viral inactivated protein-containing composition, i.e., a blood product containing a labile protein, (3) without incurring substantial protein denaturation. As shown above, these three goals are not necessarily compatible since, for example, beta-propiolactone inactivates viral infectivity, but is unsafe and substances such as formaldehyde inactivate viruses, but also substantially denature the valuable plasma proteins, for example, factor VIII.

It, therefore, became desirable to provide a process for obtaining protein-containing compositions which does not substantially denature the valuable protein components therein and which does not entail the use of a proven carcinogenic agent. More especially, it is desirable to provide blood protein-containing compositions in which substantially all of the hepatitis viruses and other viruses present are inactivated and in which denatured protein such as factor VIII account for only a small amount of the total amount of these proteins in the blood protein-containing composition.

It is a further object to provide products from cancer or normal cells or from fermentation processes following gene insertion which are substatially free of virus, especially lipid-containing viruses.

It has now been discovered, quite surprisingly, that while most of the viral inactivating agents denature factor VIII and other valuable blood plasma proteins, that not all viral inactivating agents have such effect. It has been discovered that a labile protein-containing composition, e.g., blood cell proteins, blood plasma, a blood plasma fractionation precipitate, a blood plasma fractionation supernatant, cryoprecipitate, cryosupernatant, or portion or derivative thereof or serum or a non-blood product produced from normal or cancerous cells (e.g., via recombinant DNA technology) is contacted for a sufficient period of time with a fatty acid, or a soluble ester, alcohol or a salt thereof, e.g., an alkali or alkaline earth metal salt thereof that lipid-containing viruses such as the hepatitis viruses present in the composition are virtually entirely inactivated without substantial denaturation of proteins contained therein. By contacting a blood protein mixture or concentrate thereof or fraction thereof with a fatty acid or a $C_{1-4}$ alkyl ester thereof, or alcohol thereof or a salt thereof, e.g., an alkali or alkaline earth metal salt thereof, or with a long chain unsaturated monoglyceride, hepatitis viruses can be substantially inactivated, e.g., to an inactivation of greater than 4 logs, while realizing a yield of protein activity to total protein of at least 60%.

By such procedures there is provided a labile protein-containing composition, for example, a blood protein-containing such as mammalian blood cell derivative (e.g., hemoglobin, alpha-interferon, T-cell growth factor, platelet-derived growth factor, etc.), plasminogen activator, blood plasma, blood plasma fraction, blood plasma precipitate (e.g., cryoprecipitate, ethanol supernatant or polyethylene glycol supernatant), characterized by the presence of one or more blood proteins, such as labile blood factor VIII having a total yield or protein activity to total protein of at least 60%, preferably at least 70%, said blood protein-containing composition having greatly reduced or virtually no hepatitis viruses. Virus in a serum is determined by infectivity titrations.

By the inactivation procedure of the invention, most, if not virtually all, of the hepatitis viruses contained therein are inactivated. The method for determining infectivity levels by in vivo chimpanzees is discussed by Prince, A.M., Stephen, W., Brotman, B. and van den Ende, M.C., "Evaluation of the Efect of Beta-propiolactone/Ultraviolet Irradiation (BPL/UV) Treatment of Source Plasma on Hepatitis Transmission by Factor IX Complex in Chimpanzees", *Thrombosis and Haemostasis*, 44, 138–142, 1980.

The hepatitis virus is inactivated by treatment with a fatty acid, preferably an unsaturated fatty acid, or a soluble ester, alcohol as described herein, and is not inactivated because of inclusion in the plasma of antibodies which bind with the hepatitis viruses and form immune complexes.

Inactivation of virus is obtained to the extent of at least "4 logs", i.e., virus in a serum is totally inactivated to the extent determined by infectivity studies where that virus is present in the untreated serum in such a concentration that even after dilution to $10^4$, viral activity can be measured.

BRIEF DESCRIPTION OF DRAWINGS

FIG. 3 and FIG. 4 are plots showing the inactivation of VSV added to AHF by unsaturated fatty acids after one hour (FIG. 3) and after four hours (FIG. 4).

DETAILED DESCRIPTION OF THE INVENTION

Figure 1:
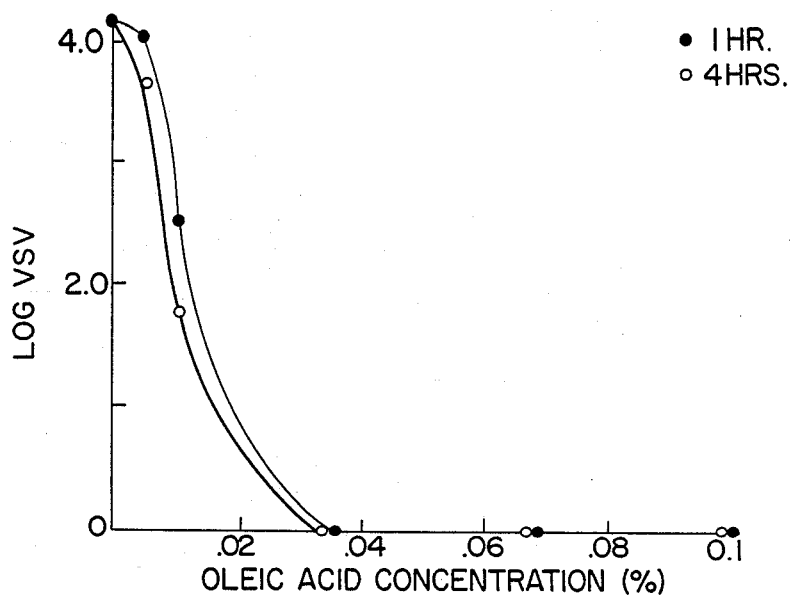
FIG. 1 is a plot of oleic acid concentration against viral infectivity.

Blood is made up of solids (cells, i.e., erythrocytes, leucocytes, and thrombocytes) and liquid (plasma). The cells contain potentially valuable substances such as hemoglobin, and they can be induced to make other potentially valuable substances, such as interferons, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

Whole blood must be carefully typed and cross matched prior to administration. Plasma, however, does not require prior testing. For certain applications, only a proper fraction of the plasma is required, such as factor VIII, for treatment of hemophilia or von Willebrand's disease.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the proteins to be concentrated, thus permitting concentrates to be treated. Of great importance, too, is the fact that the plasma fractions can be stored for much longer periods than whole blood and they can be distributed in the liquid, the frozen, or the dried state. Finally, it allows salvaging from blood banks the plasma portions of outdated whole blood that is unsafe for administration as whole blood.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor, factor IX, fibrin-stabilizing factor-factor XIII, fibrinogen), immunoglobins (immunoglobulins G, A, M, D, and E), and the complement components. There are currently more than 100 plasma proteins that have been described. A comprehensive listing can be found in "The Plasma Proteins", ed. Putnam, F.W., Academic Press, New York (1975).

Proteins found in the blood cell fraction include hemoglobin, fibronectin, fibrinogen, enzymes of carbohydrate and protein metabolism, and products of blood cells, e.g., elastase, etc. In addition, the synthesis of other proteins can be induced, such as interferons and growth factors.

A comprehesive list of inducible leukocyte proteins can be found in Stanley Cohen, Edgar Pick, J. J. Oppenheim, "Biology of the Lymphokines", Academic Press, N.Y. (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromatographic processes. An excellent survey of blood fractionation appears in *Kirk-Othmer's Encylopedia of Chemical Technology*, Third Edition, Interscience Publishers, Volume 4, pages 25 to 62, the entire contents of which are incorporated by reference herein.

The major components of a cold ethanol fractionation are as follows:

| Fraction | Proteins |
| --- | --- |
| I | fibrinogen, cold insoluble globulin; factor VII; properdin |
| II and III | IgG; IgM; IgA; fibrinogen; beta-lipoprotein; prothrombin; plasminogen; plasmin inhibitor; factor V; factor VII; factor IX; factor X; thrombin; antithrombin; isoagglutinins; ceruloplasmin; complement C'1, C'3 |
| IV-1 | alpha$_1$-lipoprotein, ceruloplasmin; plasmin inhibitor; factor IX; peptidase; alpha-and-beta-globulins |
| IV-4 | transferrin; thyroxine binding globulin; serum esterase; alpha$_1$-lipoprotein; albumin; alkaline phosphatase |
| V | albumin; alpha-globulin |
| VI | alpha$_1$-acid glycoprotein; albumin |

The above fractionation scheme can serve as a basis for further fractionations. Fraction II and III, for example, can be further fractionated to obtain immune serum globulin (ISG).

Another fractionation scheme involves the use of frozen plasma which is thawed yielding a cryoprecipitate containing AHF (antihemophilic factor), fibronectin and a cryosupernatant. The cryoprecipitate is then fractionated into fibronectin and AHF.

Polyethylene glycol has been used to prepare high purity AHF and non-aggregated ISG.

High risk products with respect to the transmission of hepatitis B and non-A, non-B are fibrinogen, AHF and prothrombin complex, and all other blood protein preparations, except intramuscular immune serum globulin and, because they are pasteurized, albumin solutions. Hepatitis tests presently available can indicate the presence of hepatitis B surface antigen, but there is presently no screening test for non-A, non-B hepatitis.

The present invention is directed to contacting with a saturated or unsaturated fatty acid or with a soluble ester, alcohol or salt thereof, a blood protein-containing composition, such as mammalian blood cell proteins, blood plasma thereof, precipitate from any fractionation of such plasma, supernatant from any fractionation of such plasma, cryoprecipitate, cryosupernatant or any portions or derivatives of the above that contain blood proteins such as, for example, prothrombin complex (factors II, VII, IX and X) and cryoprecipitate (factors I and VIII).

The present invention is particularly effective for AHF concentrate, prothrombin complex concentrate, immune globulin solution and anti-thrombin III (AT-III) concentrate.

Such protein-containing composition is contacted with a fatty acid, or a soluble ester, alcohol or salt, e.g, an alkali or alkaline earth metal salt thereof. When an esterified form of the fatty acid is employed, the ester group has an alkyl radical which contains, 1 to 4 carbon atoms, especially a methyl or ethyl group. Particularly, contemplated salts include the sodium and potassium salts, particularly the sodium salt.

Non-limiting examples of fatty acids for use in the present invention include oleic acid, 11-eicosenic acid, arachidonic acid, linoleic acid, linolenic acid, palmitoleic acid, elaidic acid, gamma-linolenic acid, palmitic acid and arachidic acid.

The fatty acid for use in the present invention should be sufficiently soluble in an aqueous environment utilized so as to provide the necessary reagent concentration. It is preferred that the fatty acid have one double bond, preferably in the "cis" configuration. Preferably, the fatty acid should have 16 to 20 carbon atoms.

A glyceride of a fatty acid is one form of an ester that may be used in the present invention. Particularly preferred is a long chain unsaturated monoglyceride such as 1-monooleyl-rac-glycerol.

Utilization of fatty acids for the preparation of therapeutic derivatives is favorable because they are naturally occurring, because they have a low potential for toxicity, and because once introduced into the product, they might not need to be removed, thus simplifying the overal process.

The fatty acid, soluble ester, alcohol or salt can be used with or without the addition of wetting agents. It is possible, however, to use a fatty acid, or ester, alcohol or salt thereof in conjunction with a wetting agent. Such wetting agent can be added either before, simultaneously with, or after the fatty acid or a soluble ester, alcohol or salt thereof contacts the blood protein-containing composition. The function of the wetting agent is to enhance the contact of the virus in the blood protein-containing composition with the fatty acid, soluble ester, alcohol or salt thereof. The wetting agent alone does not adequately inactivate the virus.

Preferred wetting agents are non-toxic detergents. Contemplated non-ionic detergents include those which disperse at the prevailing temperature at least 0.1% by weight of the fat in an aqueous solution containing the same when 1 gram detergent per 100 ml of solution is introduced therein. In particular there is contemplated detergents which include polyoxyethylene derivatives of fatty acids, partial esters of sorbitol anhydrides, for example, those products known commercially as "TWEEN 80", "TWEEN 20" and "POLYSORBATE 80" and non-ionic oil soluble water detergents, such as that sold commercially under the trademark "TRITON X 100" (oxyethylated alkylphenol). Also contemplated are bile salts such as sodium deoxycholate, as well as the "Zwittergents" which are synthetic zwitterionic detergents known as "sulfobetaines" such as N-dodecyl-N, N-dimethyl-2-ammonio-1 ethane sulphonate and its congeners or non-ionic detergents, such as octyl-beta-D-glucopyranoside.

Substances which might enhance the effectiveness of oleic acid compounds include reducing agents, such as mercaptoethanol, dithiothreitol, dithioerythritol, and dithiooctanoic acid. Suitable non-ionic surfactants are oxyethylated alkyl phenols, polyoxyethylene sorbitan fatty acid esters, polyoxyethylene acids, polyoxyethylene alcohols, polyoxyethylene oils and polyoxyethylene oxypropylene fatty acids. Some specific examples are the following:

alkylphenoxypolyethoxy (3) ethanol
polyoxyethylene (2) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) lauryl ether
polyoxyethylene (20) cetyl ether
polyoxyethylene (20) stearyl ether
polyoxyethylene (25) oleyl ether
polyoxyethylene (25) hydrogenated castor oil and
polyoxyethylene (25) oxypropylene monostearate The amount of wetting agent, if employed, is not crucial, for example, from about 0.001% to about 10%, preferably about 0.01 to 1.5% , can be used.

Di-and trialkylphosphates as described in U.S. Pat. No. 4,540,573 and Ser. No. 631,675, filed July 17, 1984, now pending, may be used in conjunction with the fatty acid compounds or long chain unsaturated monoglycerides, which can also be used in conjunction with other inactivating agents, such as alcohol or ethers, with or without the copresence of wetting agents in accordance with U.S. Pat. No. 4,481,189, the entire contents of which are incorporated by reference herein.

The ether or alcohol can be added in an amount of 1 to 50%, preferably 5 to 25% by weight, based on the volume of blood plasma, or concentrate or other blood plasma protein-containing composition to be treated.

Particularly contemplated ethers for inactivation use in accordance with the invention are those having the formula $$R^1—O—R^2$$

wherein $R^1$ and $R^2$ are independently $C_1$–$C_{18}$ alkyl or alkenyl which can contain an O or S atom in the chain, preferably $C_1$ to $C_8$ alkyl or alkenyl. Especially contemplated ethers are dimethyl ether, diethyl ether, ethyl propyl ether, methyl-butyl ether, methyl isopropyl ether and methyl isobutyl ether.

Alcohols contemplated include those of the formula $$R^3OH$$

wherein $R^3$ is a $C_1$ to $C_{18}$ alkyl or alkenyl radical which can contain one or more oxygen or sulfur atoms in the chain and which can be substituted by one or more hydroxyl groups.

Especially contemplated alcohols are those where the alkyl or alkenyl group is between 1 and 8 atoms. Particularly contemplated alcohols include methanol, ethanol, propanol, isopropanol, n-butanol, isobutanol, n-pentanol and the isopentanols. Also contemplated are compounds such as ethylene glycol, 1,2-propylene glycol, 1,3-propane diol, 1,4-butanediol, 2-hydroxy isobutanol (2-methyl, 1,2-dihydroxypropane).

Treatment of labile protein-containing compositions with trialkylphosphate is effected at a temperature between −5° C. and 70°, preferably between 0° C. and 60° C. The time of such treatment (contact) is for at least 1 minute, preferably at least 1 hour and generally 4 to 24 hours. The treatment is normally effective at atmospheric pressure, although subatmospheric and superatmospheric pressures can also be employed.

Normally, after the treatment, the fatty acid or soluble ester, alcohol or salt thereof and other inactivating agents, for example, ether, are removed, although such is not necessary in all instances depending upon the nature of the virus inactivating agents and the intended further processing of the blood plasma protein-containing composition.

To remove ether from plasma, the plasma is generally subjected to a temperature of 4° C. to 37° C. with a slight vacuum imposed to draw off residual ether. Preferably means are provided to spread the plasma as a thin film to insure maximum contact and removal of the ether. Other methods for removal of ether in activating agents include:

(1) bubbling of nitrogn gas;

(2) diafiltration using ether insoluble, e.g., "TEFLON", microporous membranes which retain the plasma proteins;

(3) absorption of desired plasma components on chromatographic or affinity chromographic supports;

(4) precipitation, for example, by salting out of plasma proteins;

(5) lyophilization, etc.

When alcohol or non-ionic detergents are employed with the oleic acid compounds they are removed by (2) to (5) above.

Di-or trialkylphosphate can be removed as follows:

(a) Removal from AHF can be effected by precipitation of AHF with 2.2 molal glycine and 2.0 M sodium chloride (b) Removal from fibronectin can be effected by binding the figronectin on a column of insolubilized gelatin and washing the bound fibronectin free of reagent.

Alcohol is normally removed together with detergent. If the detergent includes both alcohol and ether, the ether is normally removed before the alcohol.

The process of the invention can be combined with still other modes of inactivating viruses, including those for non-lipid coated viruses. For instance, a heating step can be effected in the presence of a protein stabilizer, e.g., an agent which stabilizes the labile protein (AHF) against inactivation by heat. Moreover, the heating can be carried out using stabilizers which also tend to protect all protein, including components of the virus, against heat, if the heating is carried out for a sufficient length of time, e.g., at least 5 hours and preferably at least 10 hours at a temperature of 50 95° C., especially 60° to 70° C. By such mode, the virus is preferentially inactivated, nevertheless, while the protein retains a substantial amount, e.g., greater than or equal to 80% of its protein activity. Of course, the best treatment can also be carried out simultaneously with the fatty acid or a soluble ester, alcohol or salt thereof treatment.

The treatment of plasma or its concentrates, fractions or derivatives in accordance with the present invention can be effected using fatty acid, or a soluble ester, a alcohol or salt thereof immobilized on a solid substrate. The same can be fixed to a macro-molecular structure, such as one of the type used as a backbone for ion exchange reactions, thereby permitting easy removal of the fatty acid, or soluble ester, alcohol or salt thereof from the plasma or plasma concentrate. Alternatively, the fatty acid or a soluble alcohol or salt thereof can be insolubilized and immobilized on a solid support such as glass beads, etc., using silane or siloxane coupling agents.

The method of the present invention permits the pooling of human blood plasma and the treatment of the pooled human blood plasma in the form of such pooled plasma. It also permits the realization of blood product derivatives such as factor VIII, gamma globulin, factor IX or the prothrombin complex (factors II, VII, IX, X), fibrinogen and any other blood derivative including, all of which contain little or no residual infective hepatitis or other viruses.

The fatty acid, or a soluble ester, alcohol or salt thereof is preferably employed in a concentration of a least 0.02 weight percent, generally 0.025 to 0.1 weight percent. Concentrations higher than 0.4 weight percent do not appear to provide improved virus inactivation as at the lower concentrations of 0.02 to 0.4, especially about 0.035 the degree of viral inactivity is such that virus is undetectable or substantially undetectable.

The fatty acid or a soluble ester, alcohol or salt thereof treatment is effected for up to about 24 hours. However, shorter treatment periods are preferred. For AHF, treatment is conducted for about up to 5 hours as longer periods of treatment, e.g., 6 hours decrease the yield of labile protein, at least in the case of AHF when concentrations of the fatty acid, or an ester, alcohol or salt thereof of 0.1 weight percent are employed.

At fatty acid concentrations of 0.01 to 0.06 weight percent at contact times of up to about 5 hours, very acceptable AHF yields can be obtained. For instance, at a contact time of one hour using sodium oleate at an oleic acid concentration of 0.02 to 0.06, AHF yield in excess of 60% can be obtained. When the concentration is 0.02 to 0.035 the AHF yield is in excess of 70%. Using a contact time or 4 hours, one observes a greater degree of AHF yield loss. Thus, at such higher contact times, the fatty acid or a soluble ester, alcohol or salt thereof should be below about 0.038 and generally 0.020 to 0.038 weight percent.

The inactivation can be carried out at 0° to 60° C., although it is preferred at 20° to 37° C.

The present invention is directed, inter alia, to producing a blood plasma protein-containing composition such as blood plasma, blood plasma fractions, etc., which is substantially free of infectious virus, yet which contains a substantial amount of viable (undenatured) protein. More particularly, the present invention is directed to inactivation of lipid-containing virus and preferentially inactivation of hepatitis B and non-B, non-A virus. Other viruses inactivated by the present invention include, for example, cytomegaloviruses, Epstein Barr viruses, lactic dehydrogenase viruses, herpes group viruses, rhabdoviruses, leukoviruses, myxoviruses, alphaviruses, Arboviruses (group B), paramyxoviruses, arenaviruses, coronaviruses, and retroviruses, e.g., HTLV-III/LAV.

According to the present invention, there is contemplated a protein-containing composition - a product produced from normal or cancerous cells or by normal or cancerous cells (e.g., via recombinant DNA technology), such as mammalian blood plasma, blood plasma fractions, precipitates from blood fractionation and supernatants from blood fractionation having an extent of inactivation of virus greater than 4 logs of virus such as hepatitis B and non-A, non-B, and having a yield of protein activity to total protein of at least 70%, preferably at least 95% and most preferably 98% to 100%.

Further contemplated by the present invention is a composition containing factor VIII which is substantially free of hepatitis virus to the extent of having an inactivation of greater than 4 logs of the virus and a yield of protein activity to total protein of at least 70%, preferably at least 85%, more preferably at least 95% and most preferably 98% to 100%.

The process of the present invention has been described in terms of treatment of plasma, plasma fractions, plasma concentrates or components thereof. The process, however, is also useful in treating the lysates or proteins secreted by cells. Thus, also contemplated are treatment of fractions derived from platelets, white cells (leukocytes ), red cells, fibroblasts. Included are solutions of interferon, transfer factor, hemoglobin, and growth factors.

One can treat plasma itself according to the present invention or fresh frozen plasma, thawed frozen plasma, cryoprecipitate, cryosupernatants or concentrates from frozen plasma, as well as dilution products thereof.

By the same manipulative steps discussed above, virus present in products of normal or cancerous cells can be inactivated while retaining labile protein activity in such products. For instance, by the same fatty acid, ester or salt treatment or long chain unsaturated monoglyceride treatment one can inactivate products produced using normal or cancer cells, the exudate from normal or cancerous cells, hybridomas and products produced by gene splicing. Such treatment does not substantially adversely affect the desired protein. Cells used for production of desired protein can, of course, be mammalian, as well as non-mammalian cells.

The present invention will now be described with reference to the following non-limitative examples.

EXAMPLES

Examples 1 to 4

The conditions under which the oleic acid salt were employed in Table 1 below are not the preferred conditions. Hence, while exceptional VSV inactivation was achieved, the AHF yield was also effected, sometimes quite significantly.

Example 5

Figure 2:
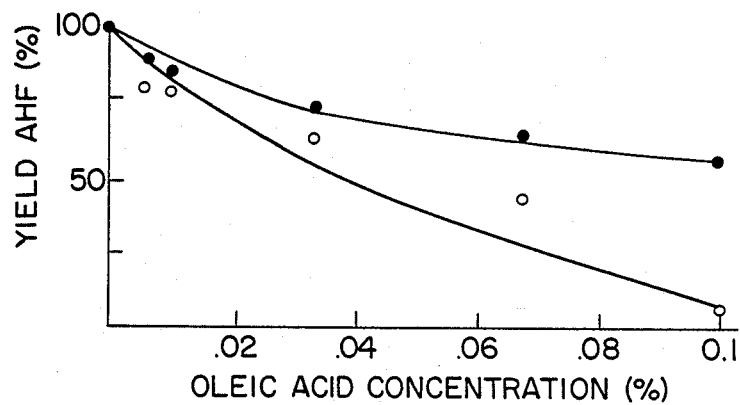
FIG. 2 is a plot of the same concentration of oleic acid as in FIG. 1 against AHF yield.

The oleic acid used for Example 5 and plotted in FIG. 1 and FIG. 2 was employed in the form of its sodium salt. AHF was used as a model blood plasma because it is considered to be one of the most labile blood proteins. VSV was chosen as a model virus as its behavior predicts the behavior of lipid-enveloped viruses, such as hepatitis B virus and for the additional reason that chimpanzee test animals are required to determine elimination of hepatitis virus.

ing elution from DEAE-Sephadex (H. G. J. Brummelhuis, *Methods of Plasma Protein Fractionation*, J. M. Curling (Ed.), (Academic Press, New York, (1980) pp. 117), were provided by the Blood Derivatives Program of the New York Blood Center. Fatty acids were obtained from Sigma Chemical Company. A 1% or 33.3% (w/v) stock solution of each was prepared in 33% or 95% ethanol.

Assay of viruses and coagulation factors were as described in B. Horowitz, M. E. Wiebe, A. Lippin and M. H. Stryker, *Transfusion*, 25, 516 (1985). Anti-hepatitis B surface antigen was determined by Ausab obtained from Abbott Laboratories.

Results:

The addition of fatty acids to an AHF concentrate containing either VSV or Sindbis virus caused a rapid and complete inactivation of virus for oleic, linoleic, linolenic, palmitoleic, arachidonic and 11-eicosenoic acids (FIG. 3, FIG. 4 and Table 2). Fatty acid, dissolved in 33% ethanol, was added to an AHF concentrate containing VSV. After 1 and 4 hours at 24° C., samples were removed, diluted 100-fold and assayed for residual virus. The fatty acid nomenclature follows that given in Table 2. For each of these fatty acids, the degree of virus kill and AHF retention depended on the fatty acid concentration used and the duration of incubation. On a weight basis, oleic acid was the most potent of the fatty

TABLE 1
EFFECT OF FATTY ACIDS ON AHF AND VSV

| Example No. | Reference Agent | Reference | Conditions Reported | Conditions Used | AHF Yield (%) | VSV Decline (log) |
|---|---|---|---|---|---|---|
| 1. | BHT | 1 | Up to 0.011%, 30 minutes, ambient temperature | 0.1%, 6 hours, ambient temperature | 100 | 0.4 |
| 2. | Linoleic Acid Na Salt | 2 | 0.001–0.01% 10–60 minutes, 25° C. | 0.01%, 6 hours, ambient temperature | 97 | 0.4 |
| 3. | Linolenyl alcohol | 3 | 0.00012%, 20 minutes, 25° C. | 0.01%, 6 hours, ambient temperature | 93 | 0.1 |
| 4. | Oleic Acid Na Salt | 2,4 | 0.001–0.01%, 10–60 minutes, 25° C. | 0.1%, 1 hour, ambient temperature | 44 | >4.2 |
|  |  |  |  | 0.1%, 6 hours, ambient temperature | 1 | >4.2 |

1. Keith, A.D. and Sniper, W., "Inactivation of Lipid Containing Viruses with Butylated Hydroxytoluene", U.S. Pat. No. 4,350,707, 1982.
2. Kohn, A., Gitelman, J., and Inbar, M., "Unsaturated Free Fatty Acids Inactivate Animal Enveloped Viruses", Arch. Virology, 66:301 (1980).
3. Sands, J., Auperin, D., and Snipes, W., "Extreme Sensitivity of Enveloped Viruses, Including Herpes Simplex, to Long-Chain Unsaturated Monoglycerides and Alcohols", Antimicrobial Agents and Chemother., 15:67 (1979).
4. Stock, C.Cl, and Francis, T. Jr., "The Inactivation of the Virus of Epidemic Influenza by Soaps", J. Exp. Med., 71:661 (1940).

Example 6

Frozen plasma anticoagulated in CPDA-1 (an anticoagulant and preservative used in blood banks; acronym for citrate, phosphate dextrose and adenine-formulation 1) and single donor cryoprecipitate solubilized in plasma were obtained from the Blood Program of the New York Blood Center, New York, New York. Cryoprecipitate was solubilized in either plasma or 0.02 M Tris, 0.02 M sodium citrate, 0.1 M sodium chloride, pH 7.2, or was obtained following reprecipitation with heparin (G. Rock, R. K. Smiley, P. Tittley, D. S. Palmer, *New England J. Med.*, 311, 310 (1984)). In process fractions of purified blood derivatives, AHF concentrate 10° C. supernatant (B. Horowitz et al, *Transfusion*, 24, 357 (1984)), Cohn fraction II prepared by ethanol precipitation (E. J. Cohn et al, *J. Am. Chen. Soc.*, 68, 459 (1946); J. L. Oncley, M. Melin, D. A. Richert, J. W. Cameron, P. M. Gross, Jr., *J. Am. Chem. Soc.*, 71, 541 (1949)), and prothrombin complex concentrate followacids tested and the degree of kill decreased according to the following order: oleic>eicosenoic, arachidonic, linoleic>linolenic>palmitoleic. Exposure for a period as brief as one hour appeared adequate in several cases. Under conditions which provided apparent complete inactivation of added virus, AHF recovery was 63% to 100%. Minimal virus kill in an AHF concentrate was achieved at a fatty acid concentration of 0.01%, a value reported previously (C. C. Stock, T. Francis, Jr., supra; A. Kohn et al, supra) to provide substantial virus inactivation in dilute culture medium. It is believed that AHF concentrate contains an inhibitor of fatty acid action since >4 $\log_{10}$ kill of virus in buffer was achieved for each of several of fatty acids.

Two unsaturated fatty acids, elaidic and gamma-linolenic, and two saturated fatty acids, palmitic and arachidic, and another fat soluble compound, butylated hydroxytoluene (BHT), were relatively less effective. Among the glycerides tested, the long chain monoglyceride, 1-monooleyl-rac-glycerol, but not the di-and tri-glycerides, diolein and triolein, displayed antiviral properties.

The effect of sodium oleate on other blood derivatives was tested. Complete virus kill was observed on incubation of 0.033% sodium oleate at 24° C. with solutions of prothrombin complex concentrate, immune globulin and anti-thrombin III (Table 3). Protein function was maintained as evidenced by recoveries approaching 100% when factor IX, anti-thrombin III, and anti-HBs activity was measured. Less virus inactivation was achieved in plasma or plasma cryoprecipitate or in an albumin solution (Table 3), probably as a result of the direct interaction between oleate and endogenous fats and albumin itself.

Of the fatty acids tested, virus kill depended on the presence of at least one double bond, preferably in the "cis" configuration. Virucidal potency of the mono-unsaturated fatty acids was enhanced by increasing the chain length from C16 to C18 or C20. For C18 fatty acids, virucidal activity decreased with increasing degree of unsaturation.

TABLE 2

TREATMENT OF AN AHF CONCENTRATE BY UNSATURATED FATTY ACIDS

| Fatty Acid | Conc. % | AHF Recovery (%) | | VSV Decline (log) | | Sindbis Decline (log) | |
|---|---|---|---|---|---|---|---|
| | | 1 hr. | 4 hrs. | 1 hr. | 4 hrs. | 1 hr. | 4 hrs. |
| None | — | — | 122 | — | 0.1 | — | 0.0 |
| Palmitic (C16:0) | 0.1 | 97 | 111 | 0.0 | 0.3 | — | — |
| | 0.3 | 86 | 91 | 0.1 | 0.1 | — | — |
| Palmitoleic (C16:1) | 0.01 | — | 89 | — | 0.3 | — | — |
| | 0.10 | 78 | 81 | 0.4 | 0.3 | 3.1 | 3.2 |
| | 0.20 | 45 | 54 | 0.5 | 3.9 | — | — |
| | 0.30 | 63 | 11 | >5.0 | >5.0 | — | — |
| Oleic (C18:1) | 0.01 | 88 | 89 | 0.2 | 0.7 | — | — |
| | 0.033 | 72 | 63 | >4.7 | >4.7 | >5.6 | >5.7 |
| | 0.10 | 44 | 1 | >4.2 | >4.2 | >5.2 | >5.2 |
| Linoleic (C18:2) | 0.01 | — | 97 | — | 0.4 | — | — |
| | 0.033 | 86 | 68 | 1.4 | 3.5 | — | — |
| | 0.066 | 80 | 33 | 4.4 | >5.0 | — | — |
| | 0.10 | 64 | 2 | >4.8 | >4.8 | >5.2 | >5.2 |
| Linolenic (C18:3) | 0.01 | — | 92 | — | 0.3 | — | — |
| | 0.10 | — | 74 | 1.2 | >4.8 | 4.0 | >5.2 |
| gamma-Linolenic [C18:3 (6,9,12)] | 0.10 | — | 78 | 0.2 | 1.0 | 3.6 | 3.7 |
| Elaidic [C18:1 ("trans")] | 0.01 | — | 84 | — | 0.2 | — | — |
| | 0.10 | — | 61 | 3.6 | 3.2 | 5.1 | 5.1 |
| Arachidic (C20:0) | 0.1 | 97 | 126 | 0.0 | 0.5 | — | — |
| | 0.3 | 97 | 104 | 0.2 | 0.2 | — | — |
| II-Eicosenoic acid (C20:1) | 0.01 | 112 | 95 | 0.0 | 0.2 | — | — |
| | 0.033 | 107 | 112 | 2.3 | 3.7 | 5.9 | 5.9 |
| | 0.066 | 97 | 96 | 4.2 | >4.3 | 6.0 | >6.2 |
| | 0.1 | 87 | 81 | >4.3 | >4.3 | — | — |
| Arachidonic (C20:4) | 0.01 | — | 89 | — | 0.0 | — | — |
| | 0.033 | 79 | 75 | 1.9 | 3.8 | — | — |
| | 0.066 | 74 | 55 | >5.0 | >5.0 | — | — |
| | 0.10 | 63 | 45 | >4.8 | >4.8 | >5.2 | >5.2 |
| BHT | 0.10 | — | 100 | — | 0.4 | — | — |
| 1-Monooleoyl-rac-glycerol | 0.1 | 112 | 120 | 2.5 | 2.5 | — | — |
| | 0.3 | 107 | 98 | 3.2 | 3.3 | — | — |
| Diolein | 0.3 | 99 | 93 | 0.0 | 0.1 | — | — |
| Triolein | 0.3 | 92 | 96 | 0.0 | 0.0 | — | — |

TABLE 3

EFFECT OF SODIUM OLEATE ON BLOOD PLASMA AND ITS DERIVATIVES

| Derivative | Incubation Conditions | | | Virus Inactivation ($\log_{10}$) | | Protein Functional Recovery | |
|---|---|---|---|---|---|---|---|
| | Temp. (°C.) | Sodium Oleate (%) | Duration (hrs.) | VSV | Sindbis | Protein | (%) |
| AHF concentrate (10 mg/mL) | 24 | 0.033 | 1 | >4.7 | — | AHF | 72 |
| | | | 4 | >4.7 | >5.2 | " | 63 |
| Prothrombin complex concentrate (14 mg/ML) | 24 | 0.033 | 6 | >4.8 | >5.3 | Factor IX | 127 |
| ISG (70 mg/mL) | 24 | 0.033 | 6 | >5.0 | >4.6 | Anti-HBs | 96 |
| Antithrombin III (4 mg/mL) | 24 | 0.033 | 6 | >4.7 | >5.3 | AT-III | 110 |
| Plasma | 24 | 0.15 | 4 | 1.0 | — | AHF | 58 |
| | 24 | 0.15 | 21 | 1.2 | — | " | — |
| | 30 | 0.033 | 21 | 1.6 | — | " | 57 |
| | 37 | 0.1 | 4 | 2.5 | — | " | 92 |
| | 37 | 0.15 | 4 | 3.7 | — | " | 39 |
| | 37 | none | 4 | 2.3 | — | " | 103 |
| Plasma-solubilized cyroprecipitate | 24 | 0.15 | 4 | 1.5 | — | AHF | 75 |
| | 24 | 0.15 | 21 | 1.9 | — | " | — |
| Buffer-solubilized cryoprecipitate (48 mg/mL) | 24 | 0.033 | 4 | 1.2 | — | AHF | 87 |

TABLE 3-continued
EFFECT OF SODIUM OLEATE ON BLOOD PLASMA AND ITS DERIVATIVES

| Derivative | Incubation Conditions | | | Virus Inactivation ($\log_{10}$) | | Protein Functional Recovery | |
|---|---|---|---|---|---|---|---|
| | Temp. (°C.) | Sodium Oleate (%) | Duration (hrs.) | VSV | Sindbis | Protein | (%) |
| (18 mg/mL) | 30 | 0.033 | 4 | 1.3 | 2.9 | " | 83 |
| (18 mg/mL) | 30 | 0.10 | 4 | — | — | " | 36 |
| Heparin-precipitated AHF | | | | | | | |
| (36 mg/mL) | 37 | 0.033 | 6 | 1.6 | — | AHF | 92 |
| (17 mg/mL) | 37 | 0.033 | 6 | 3.0 | — | " | 50 |
| Albumin | | | | | | | |
| (63 mg/mL) | 24 | 0.033 | 6 | 1.3 | 0.0 | — | — |
| (11.5 mg/mL) | 24 | 0.033 | 4 | 0.0 | 0.0 | — | — |
| (5.7 mg/mL) | 24 | 0.033 | 4 | >4.5 | — | — | — |

It will be appreciated that the instant specification and claims are set forth by way of illustration and not limitation, and that various modifications and changes may be made without departure from the spirit and scope of the present invention.

What is claimed is:

1. A process for rendering a labile protein-containing composition substantially free of lipid-containing viruses without incurring substantial protein denaturation, comprising contacting said composition with an effective amount of fatty acid having at least 16 carbon atoms or a salt or a monoglyceride thereof for a sufficient period of time and at a temperature of 0° C. to 37° C.

2. A process according to claim 1, wherein the fatty acid is unsaturated.

3. A process according to claim 1, wherein the fatty acid has 16 to 20 carbon atoms.

4. A process according to claim 1, wherein the fatty acid has at least one double bond in the cis configuration 5. A process according to claim 1, wherein said fatty acid is selected from the group consisting of 11-eicosenoic acid, arachidonic acid, linoleic acid, linolenic acid, palmitoleic acid, elaidic acid, linolenic acid, gamma-linolenic acid, palmitic acid and arachidic acid.

6. A process according to claim 1, wherein said salt is an alkali or alkaline earth metal salt.

7. A process according to claim 1, wherein said contacting is conducted in the presence of a wetting agent.

8. A process according to claim 7, wherein said wetting agent is a non-ionic detergent.

9. A process according to claim 7, wherein said wetting agent is added to said blood composition prior to contacting said blood product with said fatty acid or salt or monoglyceride thereof.

10. A process according to claim 7, wherein said wetting agent is added simultaneously with said fatty acid or salt or monoglyceride thereof to said blood composition.

11. A process according to claim 7, wherein said wetting agent is added after said fatty acid or salt or monoglyceride thereof contacts said protein-containing composition.

12. A process according to claim 8, wherein said detergent is a partial ester of sorbitol anhydrides.

13. A process according to claim 1, further comprising conducting said contacting in the presence of an inactivating agent selected from the group consisting of ethers and alcohols.

14. A process according to claim 7, further comprising conducting said contacting in the presence of an inactivation agent selected from the group consisting of ethers and alcohols.

15. A process according to claim 1, wherein said composition is selected from the group consisting of blood plasma, a plasma concentrate, a precipitate from any fractionation of such plasma, a supernatant from any fractionation of said plasma, a serum, a cryoprecipitate, a cell lysate, and proteins induced in blood cells.

16. A process according to claim 1, wherein said composition contains one or more proteins selected from the group consisting of fibrinogen, factor II, factor VII, factor VIII, factor IX, factor X, factor I, immunoglobins, prealbumin, retinol-binding protein, albumin, alpha-globulins, beta-globulins, gamma-globulins, factor III and the complement components, fibronectin, antithrombin III, hemoglobin, interferon, T-cell growth factor and plasminogen activator.

17. A process according to claim 1, wherein said composition is selected from the group consisting of AHF concentrate, prothrombin complex concentrate, immune globulin concentrate and anti-thrombin III concentrate.

18. A process according to claim 1, wherein said period of time is between about 1 and 5 hours.

19. A process according to claim 1, wherein said fatty acid or salt or monoglyceride thereof is employed in a concentration of between about 0.02 weight percent and about 0.1 weight percent.

20. A process according to claim 19, wherein said fatty acid or salt or monoglyceride thereof is employed in a concentration of between 0.02 weight percent and 0.04 weight percent for 1-4 hours at room temperature.

21. A process according to claim 19, wherein said composition comprises factor VIII.

22. A process according to claim 19, wherein said composition comprises factor IX.

23. A process according to claim 1, wherein the composition is selected from the group consisting of a product of a non-blood normal cell, a non-blood cancerous cell and a product of gene splicing.

24. A process according to claim 1, wherein the monoglyceride is a long chain unsaturated monoglyceride.

25. A process according to claim 24, wherein the monoglyceride is 1-monooleyl-rac-glycerol.

26. A composition produced by a process according to claim 1, wherein said composition has an extent of inactivation of virus of greater than 4 logs of virus and has a yield of protein activity to total protein of at least 70%.

27. A composition produced by a process according to claim 23, wherein the yield of protein activity to total protein is at least 95%.

28. A composition produced by a process according to claim 23, wherein the yield of protein activity to total protein is 98% to 100%.

* * * * *

UNITED STATES PATENT AND TRADEMARK OFFICE
CERTIFICATE OF CORRECTION

PATENT NO. : 4,841,023
DATED : Jun. 20, 1989
INVENTOR(S) : Horowitz

It is certified that error appears in the above-identified patent and that said Letters Patent is hereby corrected as shown below:

Title Page, under "U.S. Patent Documents", line 17     Correct spelling of --Weed--

Col. 4, line 32     Insert --contemplate the use-- after "4,314,997"

Col. 6, line 23     Correct spelling of --Effect--
Col. 9, line 6     Correct spelling of --overall--
Col. 11, line 26     Insert --to-- before "95"

Signed and Sealed this

Second Day of October, 1990

Attest:

HARRY F. MANBECK, JR.

*Attesting Officer*     *Commissioner of Patents and Trademarks*